(12) United States Patent
Morimoto

(10) Patent No.: US 10,874,284 B2
(45) Date of Patent: Dec. 29, 2020

(54) DISPLAY CONTROL DEVICE, DISPLAY DEVICE, SURGICAL ENDOSCOPIC SYSTEM AND DISPLAY CONTROL SYSTEM

(71) Applicant: SONY CORPORATION, Tokyo (JP)

(72) Inventor: Toshiyasu Morimoto, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 173 days.

(21) Appl. No.: 15/118,344

(22) PCT Filed: Feb. 13, 2015

(86) PCT No.: PCT/JP2015/000673
§ 371 (c)(1),
(2) Date: Aug. 11, 2016

(87) PCT Pub. No.: WO2015/125447
PCT Pub. Date: Aug. 27, 2015

(65) Prior Publication Data
US 2017/0172381 A1 Jun. 22, 2017

(30) Foreign Application Priority Data

Feb. 21, 2014 (JP) .................. 2014-032008

(51) Int. Cl.
*A61B 1/00* (2006.01)
*G02B 27/01* (2006.01)
(Continued)

(52) U.S. Cl.
CPC ........ *A61B 1/0005* (2013.01); *A61B 1/00055* (2013.01); *A61B 34/25* (2016.02);
(Continued)

(58) Field of Classification Search
CPC .............. A61B 1/0005; A61B 1/00055; A61B 2090/365; A61B 2090/502; A61B 34/25;
(Continued)

(56) References Cited

U.S. PATENT DOCUMENTS 9,710,968 B2 * 7/2017 Dillavou ............... G06T 19/006
2011/0046459 A1 * 2/2011 Zhang ................ A61B 5/14553
600/310
(Continued)

FOREIGN PATENT DOCUMENTS

JP          6-62438 A      3/1994
JP          2001-104331    4/2001
(Continued)

OTHER PUBLICATIONS

Jeremy T. Aidlen et al., "Head-Motion-Controlled Video Goggles: Preliminary Concept for an Interactive Laparoscopic Image Display (i-LID)" Journal of Laparoendoscopic & Advanced Surgical Techniques. Aug. 2009, 19(4): 595-598. https://doi.org/10.1089/lap.2009.0123 vol. 19 Issue 4: Aug. 11, 2009.*
(Continued)

*Primary Examiner* — Thai Q Tran
*Assistant Examiner* — Stephen R Smith
(74) *Attorney, Agent, or Firm* — Xsensus, LLP

(57) ABSTRACT

There is provided a device (200) that generates display data to be displayed by each of a plurality of head mounted displays (100A, 100B) configured to be worn by each of a plurality of users involved in a surgery based on information that the each of a plurality of users in the surgery visually recognizes.

20 Claims, 8 Drawing Sheets

(51) Int. Cl.
  *A61B 90/00*  (2016.01)
  *A61B 34/00*  (2016.01)
  *A61B 90/50*  (2016.01)
  *G06F 3/14*  (2006.01)
(52) U.S. Cl.
  CPC .............. *A61B 90/36* (2016.02); *A61B 90/50* (2016.02); *G02B 27/017* (2013.01); *G06F 3/1454* (2013.01); *A61B 2090/365* (2016.02); *A61B 2090/368* (2016.02); *A61B 2090/502* (2016.02)
(58) Field of Classification Search
  CPC ...... A61B 90/36; A61B 90/50; G02B 27/017; G06F 3/1454
  USPC ............ 348/65; 709/206; 345/156, 633, 629
  See application file for complete search history.

(56) References Cited

U.S. PATENT DOCUMENTS

| | | | |
|---|---|---|---|
| 2011/0276058 A1* | 11/2011 | Choi | B25J 9/1671 606/130 |
| 2014/0118225 A1 | 5/2014 | Jerauld | |
| 2014/0184496 A1* | 7/2014 | Gribetz | G02B 27/017 345/156 |
| 2014/0306866 A1* | 10/2014 | Miller | G06T 19/006 345/8 |
| 2015/0070389 A1 | 3/2015 | Goto et al. | |
| 2015/0304253 A1* | 10/2015 | Lee | H04L 29/06476 709/206 |
| 2015/0363979 A1* | 12/2015 | Takano | A61B 6/461 345/633 |
| 2016/0154620 A1* | 6/2016 | Tsuda | G06F 19/3481 345/633 |

FOREIGN PATENT DOCUMENTS

| | | |
|---|---|---|
| JP | 2001-117046 | 4/2001 |
| JP | 2004-062756 | 2/2004 |
| JP | 2008-154192 A | 7/2008 |
| JP | 2009-95598 | 5/2009 |
| JP | 2010-528354 | 8/2010 |
| JP | 2010-250789 | 11/2010 |
| JP | 2013-106752 A | 6/2013 |
| WO | WO 2003-042968 A1 | 5/2003 |
| WO | WO 2012/133172 A1 | 10/2012 |
| WO | WO 2013/145536 A1 | 10/2013 |

OTHER PUBLICATIONS

Muratore et al. "Image display in endoscopic surgery" Journal of the Society for Inforamtion Display, vol. 15, Issue 6, Jun. 2007, pp. 349-356.*

International Search Report dated May 12, 2015, in PCT/JP2015/000673 filed Feb. 13, 2015.

Anonymous: "Riftmax Theater 4D Multiplayer Cinema—Latest Updates 0.415", Work in Progress, Oculus VR Forums, (Jun. 13, 2013, https://forums.oculus.com/viewtopic.php?t=1636, and "Riftmax Theater 4D Multiplayer Oculus Rift VR Cinema Experience Plays 2D, 3D, 4D Movies Facebook", (Feb. 1, 2014), https://www.youtube.com.watch?v=9L49w6soLJ4, XP054975844, pp. 1-18.

Japanese Office Action dated Jan. 10, 2017 in Patent Application No. 2014-032008 (with English translation).

Office Action for Japanese Application Serial No. 2017-243360 dated Sep. 25, 2018 with English translation.

* cited by examiner

[Fig. 1]
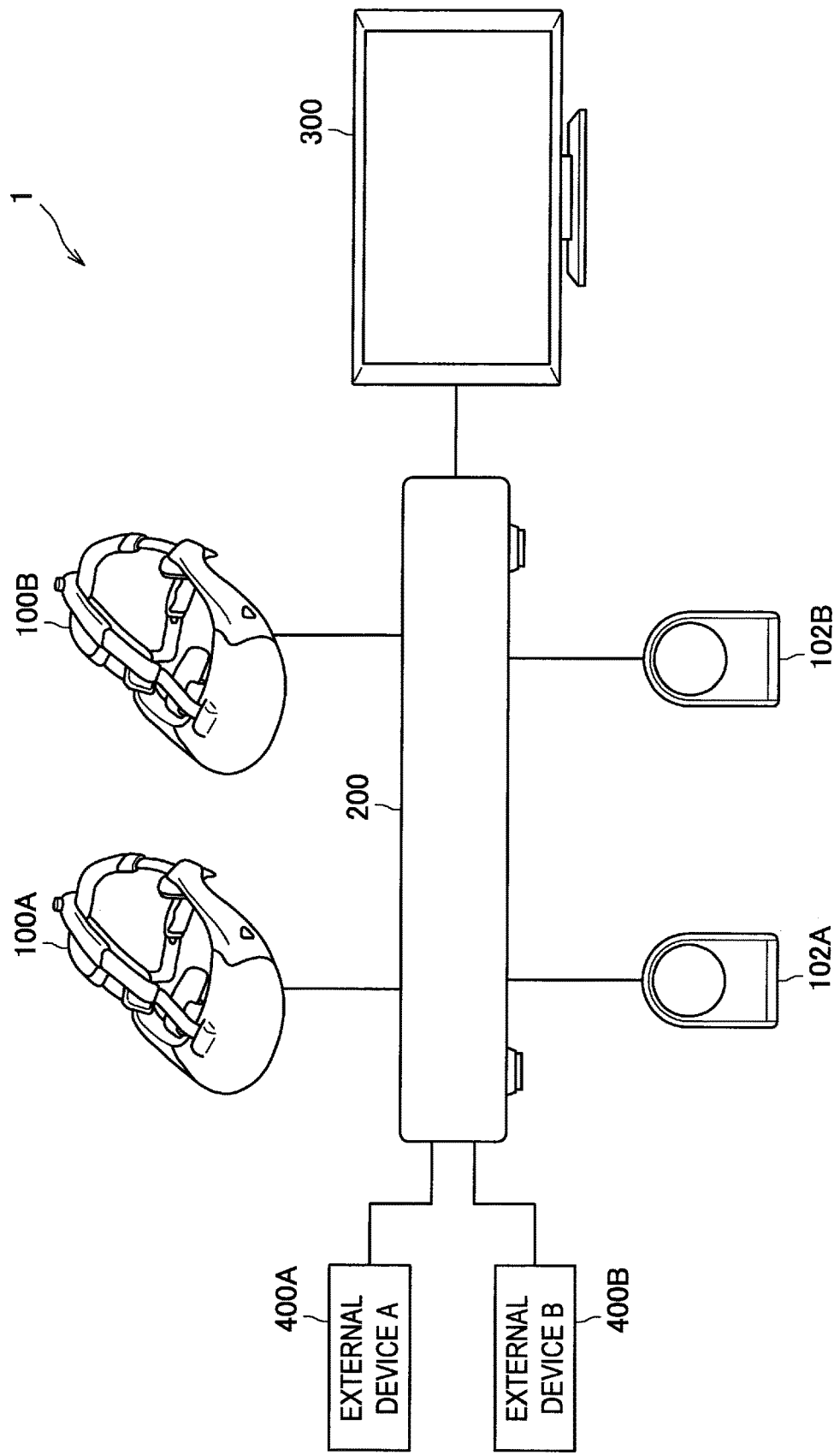

[Fig. 2]
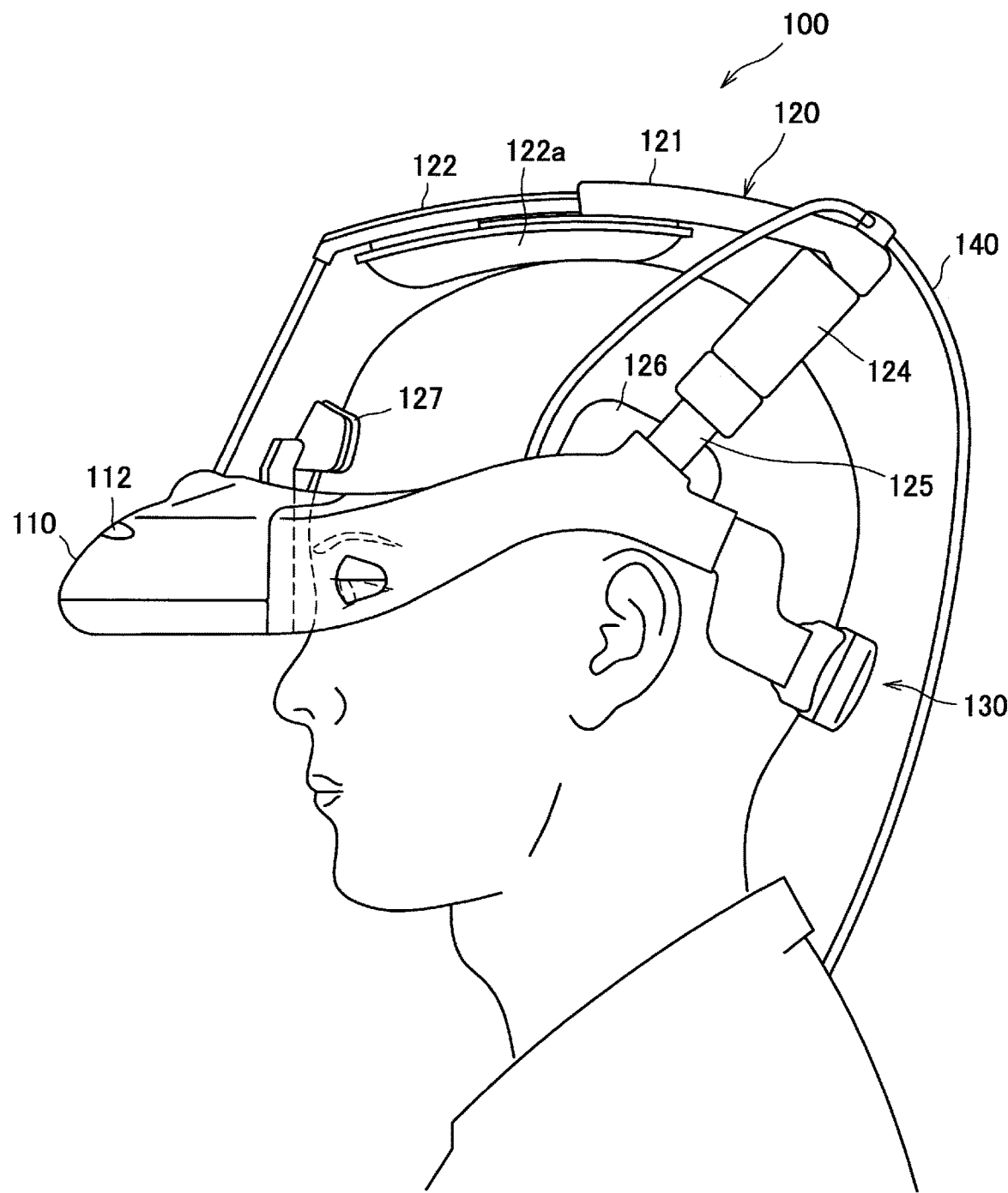

[Fig. 3]
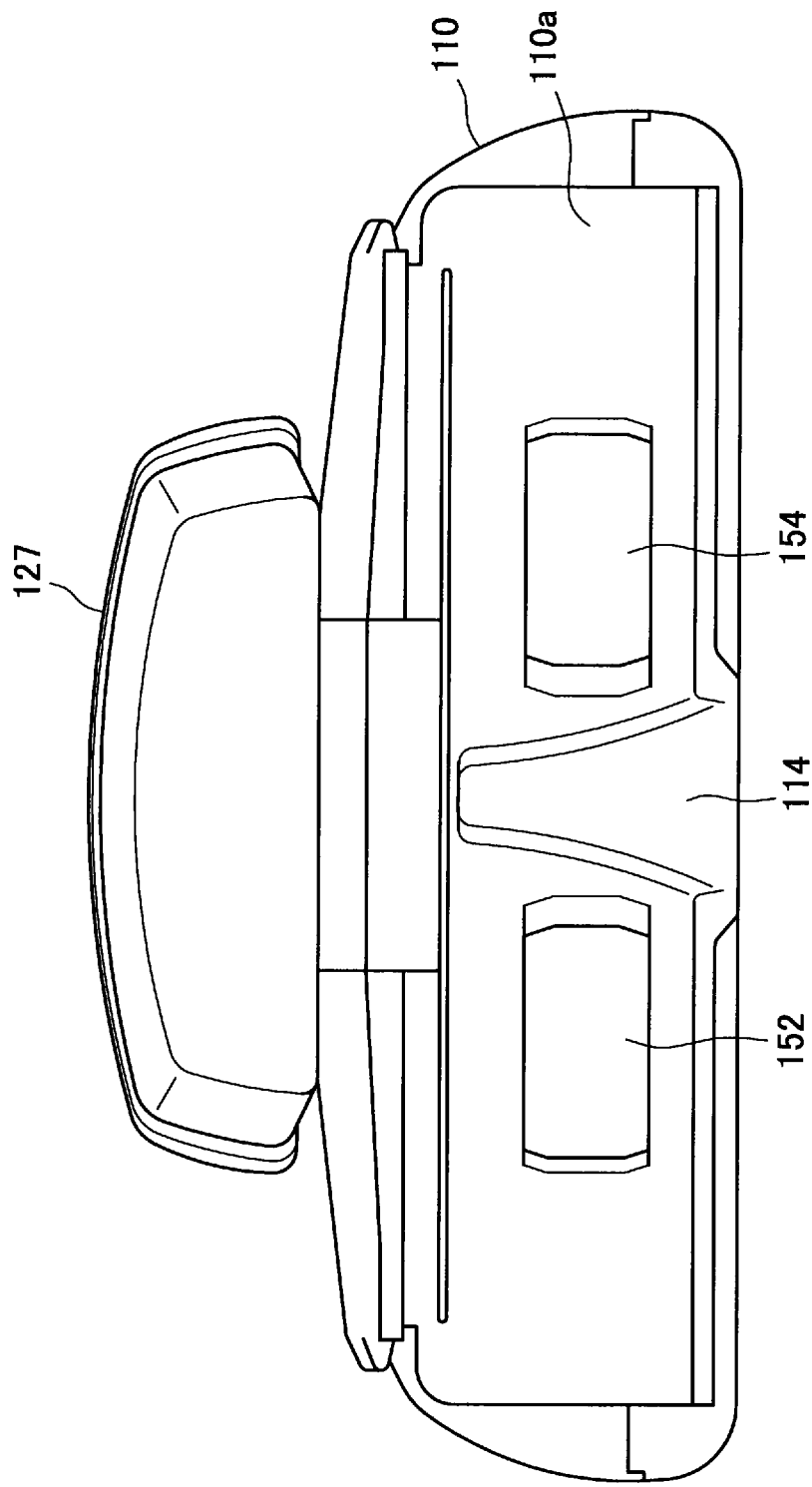

[Fig. 4]
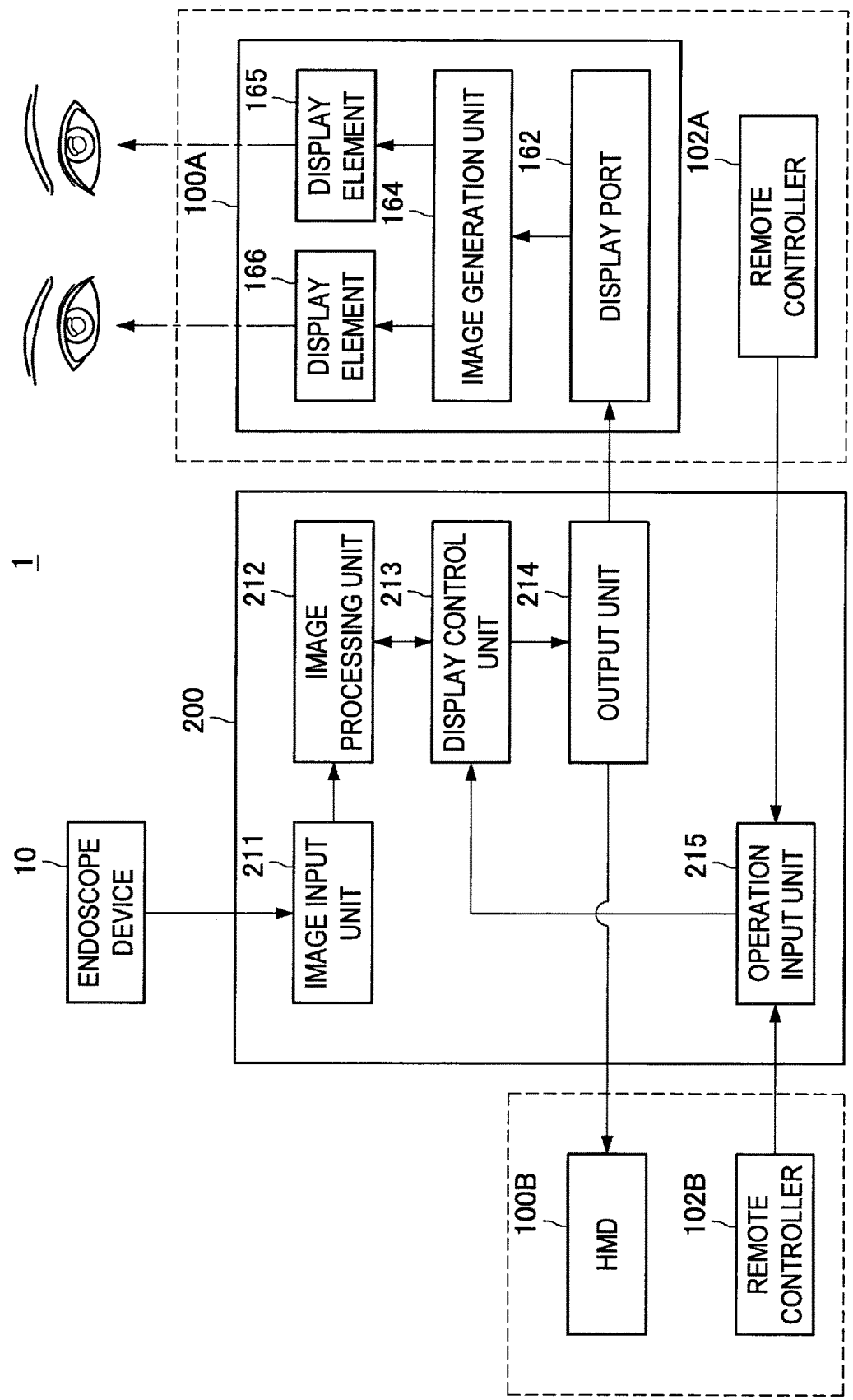

[Fig. 5]
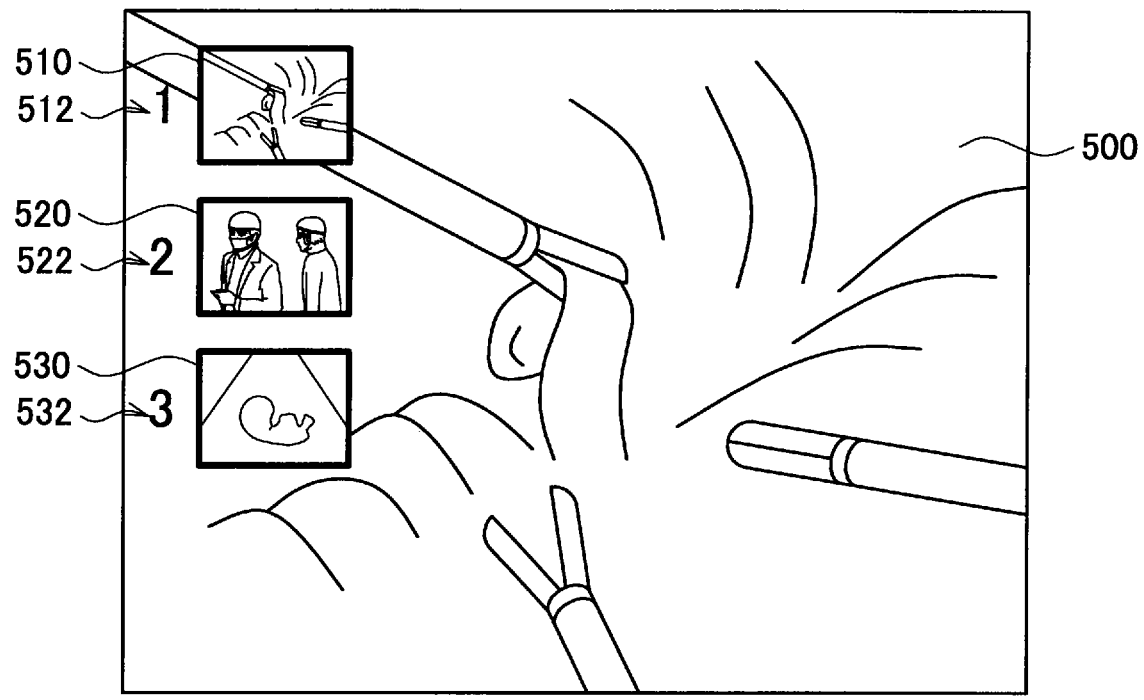
[Fig. 6]
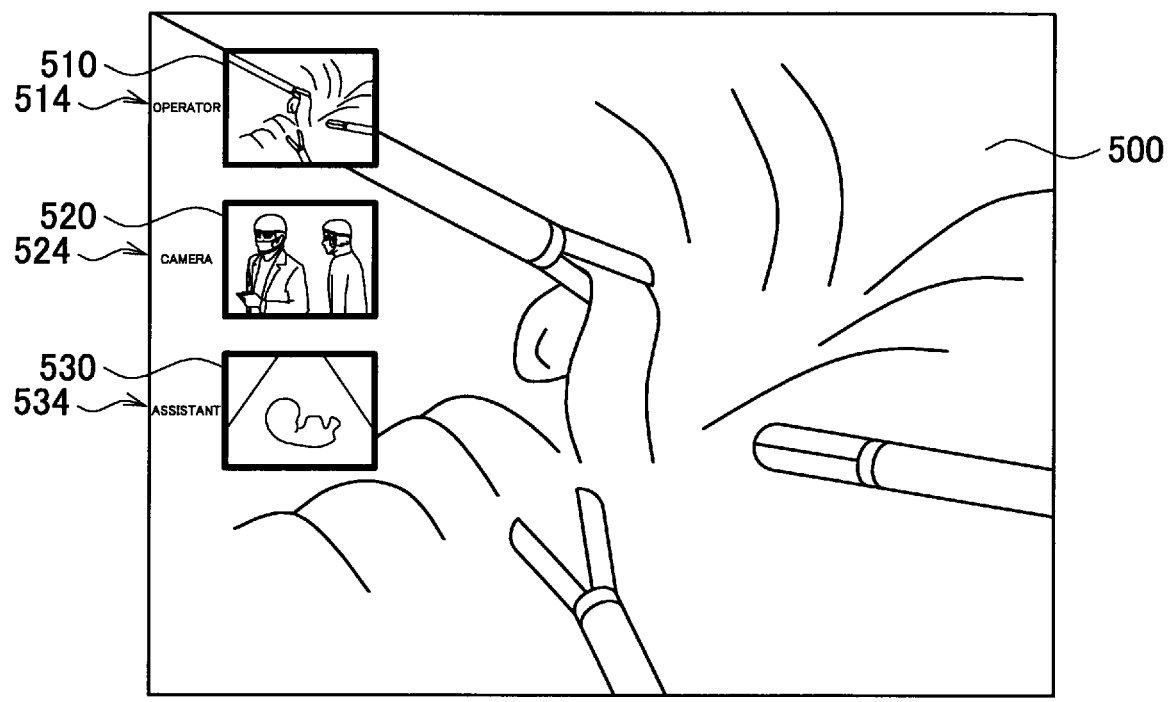

[Fig. 7]
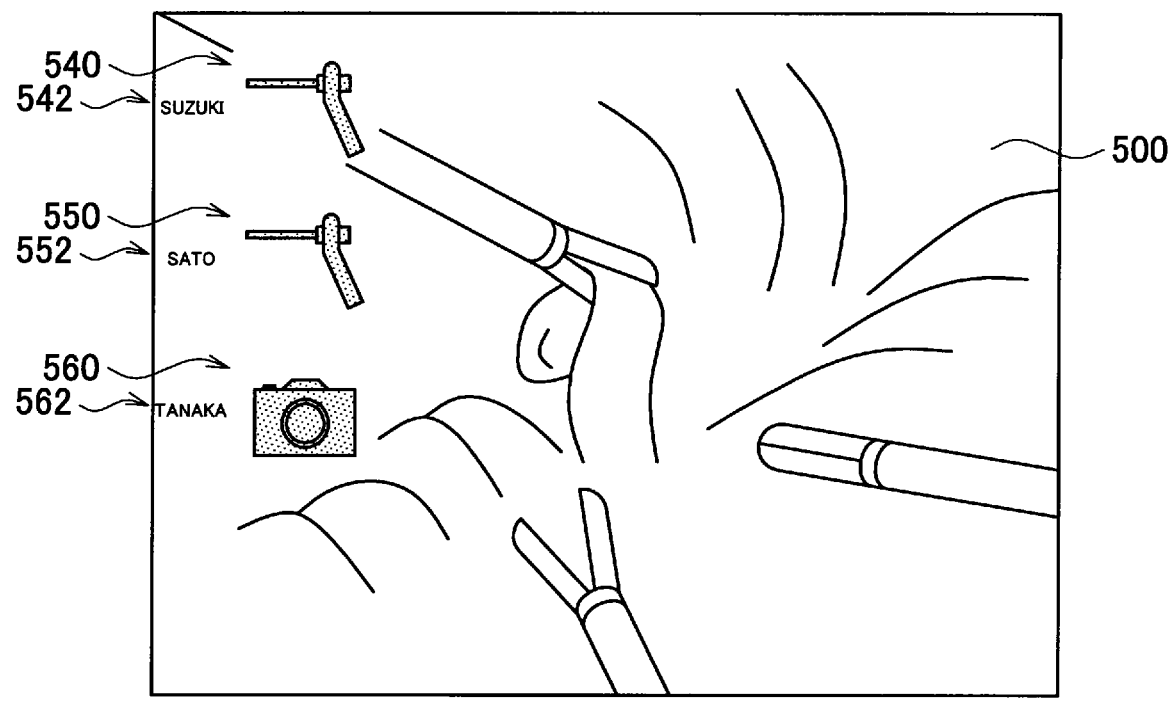

[Fig. 8]
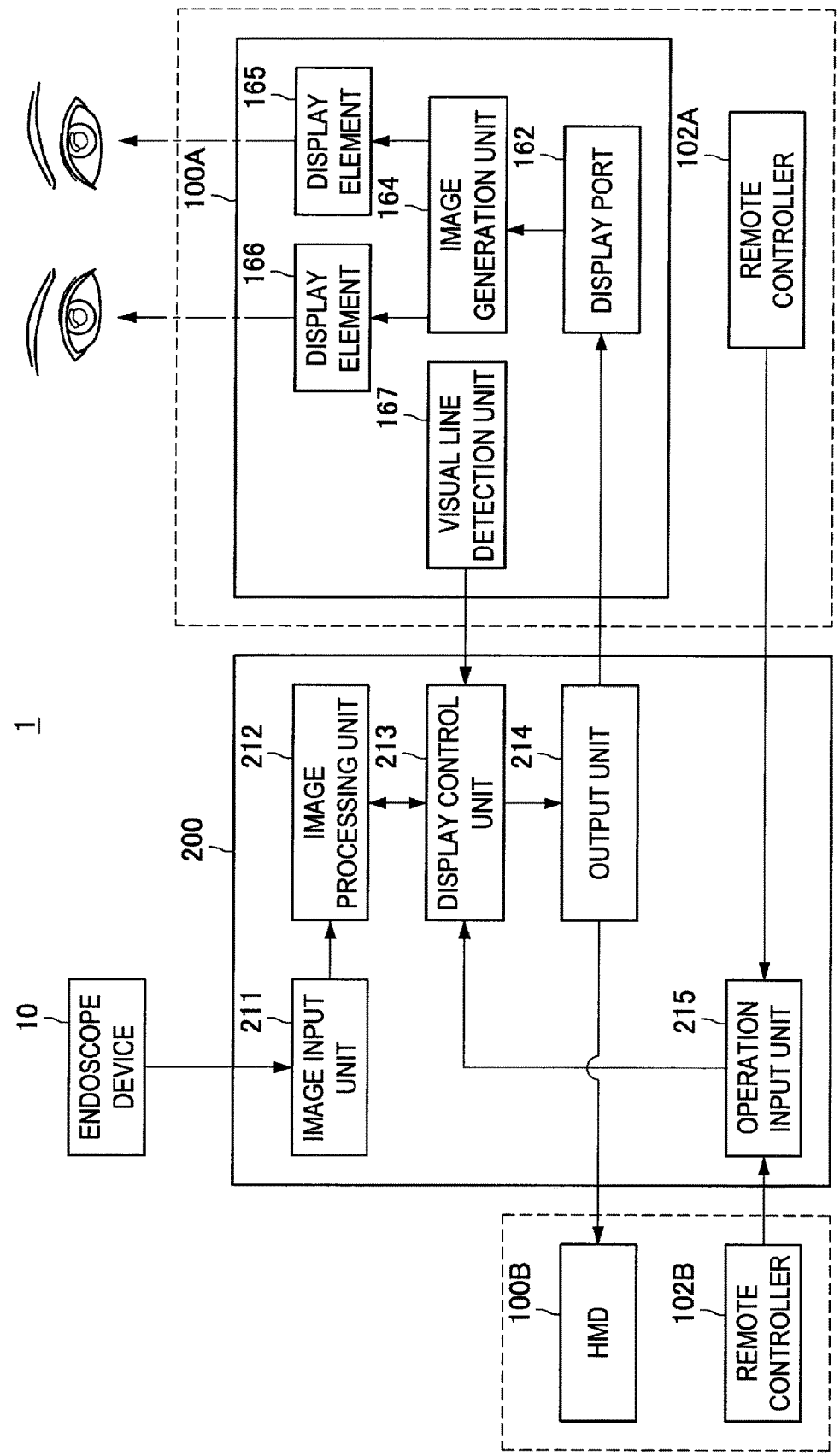

[Fig. 9]
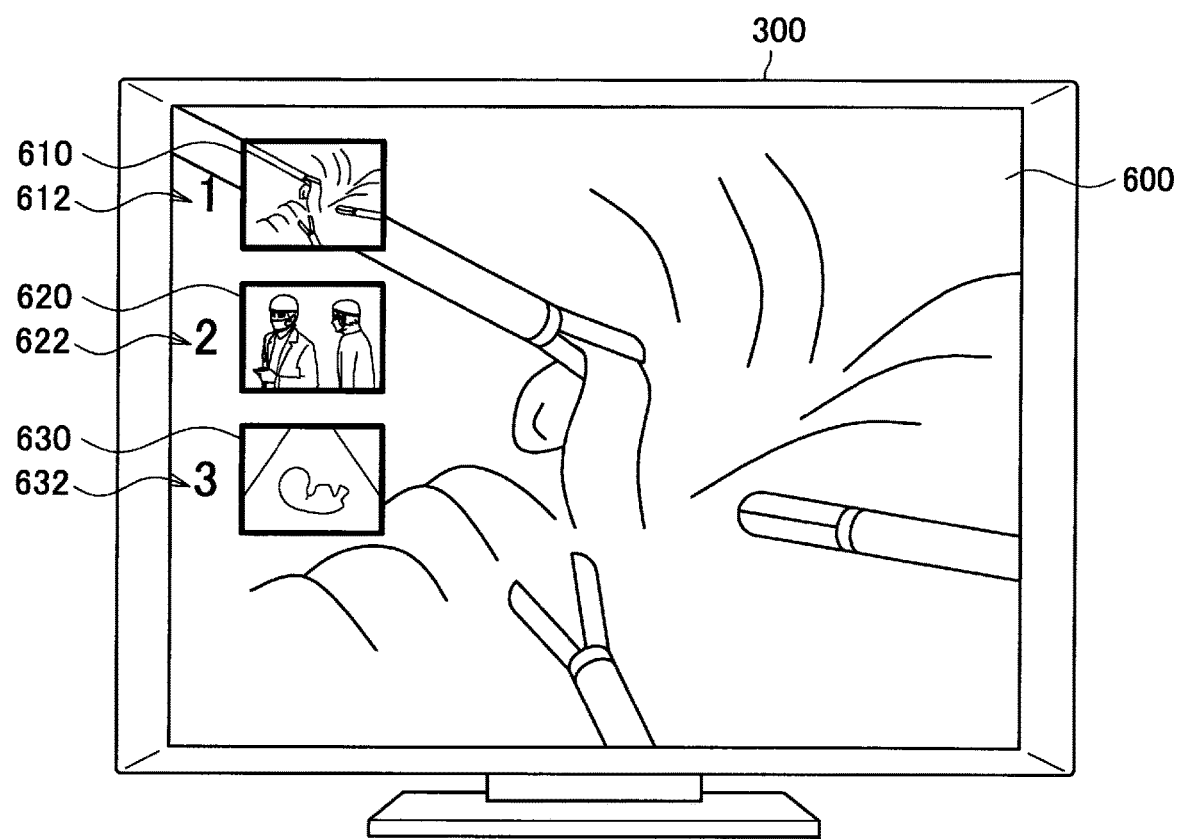

DISPLAY CONTROL DEVICE, DISPLAY DEVICE, SURGICAL ENDOSCOPIC SYSTEM AND DISPLAY CONTROL SYSTEM

CROSS REFERENCE TO RELATED APPLICATIONS

This application claims the benefit of Japanese Priority Patent Application JP 2014-032008 filed Feb. 21, 2014, the entire contents of which are incorporated herein by reference.

TECHNICAL FIELD

The present disclosure relates to a display control device that controls information to be displayed on a display device used by a plurality of users, a display device, a surgical endoscopic system and a display control system.

BACKGROUND ART

As one of wearable terminals that a user wears and uses, there is a head mounted display (hereinafter, referred to as an "HMD"). The HMD is a display device that is mounted on the head of a user when used and in recent years, the HMD is not only used as AV equipment and a display device for a computer game etc. but also used as a display device for a user to check information while working in working environment.

For example, on a medical site, the HMD is used as a display device for displaying an image of an endoscope (e.g., PTLs 1, 2). An operator wears the HMD and performs an operation while viewing an image displayed on the HMD. In the past, an image of the endoscope was usually displayed on a monitor installed in the vicinity of the operator, and therefore, it was necessary for the operator to frequently move his/her visual line between the monitor and a patient. By displaying the image of the endoscope on the HMD, it is made possible for an operator to check the image of the endoscope displayed on the display unit of the HMD and a patient without moving his/her visual line considerably.

CITATION LIST

Patent Literature

PTL 1: JP H06-062438A
PTL 2: JP 2013-106752A

SUMMARY

Technical Problem

However, when an HMD of type that covers the eyes of a person who wears the HMD is used, it is not possible to recognize peripheral environment, and therefore, it becomes difficult to establish communications during the operation, such as giving instructions to an assistant or a nurse. In contrast to this, it is conceivable to use an HMD of video see-through type that mounts a camera on the HMD to allow viewing peripheral environment. If a video see-through function is added to the HMD, an operator who is wearing the HMD is enabled to recognize the situations of staffs around the operator by switching between the endoscope image and external camera image during the operation, and therefore, it is conceivable that communication will be improved.

However, there is a case where a scopist (endoscope operator) and an assistant also wear the HMD, besides the operator. In the case such as this where a plurality of persons wears the HMDs and performs an operation in collaboration, it is possible to recognize peripheral environment by video see-through, but it is not possible to recognize what another person wearing the HMD is viewing. Because of this, there is a possibility that a loss in cooperation will occur between operators.

Consequently, the improvement in communication with another person when the HMD is mounted has been demanded.

Solution to Problem

According to the present disclosure, there is provided a display control device including a display control unit configured to display pieces of information which a plurality of users each wearing a head mounted display visually recognize, respectively, on a display unit that the respective users each wearing the head mounted display are able to visually recognize.

Further, according to the present disclosure, there is provided a display device including a display unit, and a display control unit configured to display pieces of information which a plurality of users each wearing a head mounted display visually recognize, respectively, on a display unit that the respective users each wearing the head mounted display are able to visually recognize.

Further, according to the present disclosure, there is provided a display control system including a plurality of head mounted displays, and a display control device configured to control pieces of information displayed on the head mounted displays, the head mounted displays and the display control device being communicatively connected. The display control device outputs information selected by a user wearing the head mounted display and pieces of information that the respective other users each wearing a head mounted display visually recognize to each of the head mounted displays.

According to the present disclosure, pieces of information visually recognized by users each wearing a head mounted display are displayed respectively on the display unit of each head mounted display. Due to this, it is possible for each user to recognize what other users are viewing.

Advantageous Effects of Invention

As described above, according to the present disclosure, each user is able to recognize what other users are viewing, which enables to improve the communication with other persons when each wearing the head mounted display.

The above-described effect is not necessarily limitative and it may also be possible to bring about any effect shown in the present specification or another effect that can be grasped from the present specification together with or in place of the above-described effect.

BRIEF DESCRIPTION OF DRAWINGS

FIG. 1 is a system configuration diagram showing a configuration example of an endoscope system according to a first embodiment of the present disclosure.

FIG. 2 is a schematic side view showing a state where a user wears an HMD according to the first embodiment.

FIG. 3 is a schematic diagram showing a display plane of the HMD according to the first embodiment.

FIG. 4 is a function block diagram showing a function configuration of the HMD and a processor unit constituting a display control system according to the first embodiment.

FIG. 5 is an explanatory diagram showing an example of information displayed on a display unit of the HMD and also showing an example in which thumbnails and identifiers are displayed as information of the other users.

FIG. 6 is an explanatory diagram showing another example of information displayed on the display unit of the HMD and also showing an example in which thumbnails and roles are displayed as information of the other users.

FIG. 7 is an explanatory diagram showing another example of information displayed on the display unit of the HMD and also showing an example in which objects and user names are displayed as information of the other users.

FIG. 8 is a function block diagram showing a function configuration of an HMD and a processor unit constituting a display control system according to a second embodiment of the present disclosure.

FIG. 9 is an explanatory diagram showing a display example when information viewed by each user of each HMD is displayed on a display.

DESCRIPTION OF EMBODIMENTS

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation thereof is omitted.

The following description is given in the order below.
1. First Embodiment
1.1 System Configuration
1.2 Display Control Processing
1.2.1 Function Configuration
1.2.2 Screen Display of HMD
2. Second Embodiment (example provided with a visual line detection unit)
3. Modified Examples

1. First Embodiment (1.1 System Configuration)

First, with reference to FIG. 1 to FIG. 3, as an example of a system that uses an HMD according to a first embodiment of the present disclosure, an endoscope system is described. FIG. 1 is a system configuration diagram showing a configuration example of an endoscope system 1 according to the present embodiment. FIG. 2 is a schematic side view showing a state where a user wears an HMD 100 according to the present embodiment. FIG. 3 is a schematic diagram showing display units 152 and 154 of the HMD 100.

The endoscope system 1 according to the present embodiment is a system used in an endoscopic operation and an operator wears an HMD and performs an operation while visually recognizing the state of an affected area the image of which is captured by an endoscope device.

As shown in FIG. 1, the endoscope system 1 has a configuration in which the HMDs 100 (100A, 100B), a display 300, and external devices 400 (400A, 400B) are connected to a processor unit 200.

The HMD 100 is a display device that displays information, such as input image from the external device 400. As shown in FIG. 2, the HMD 100 is, for example, a non-transmissive HMD in the shape of goggles and is used in a state of being mounted on the head of a user. The HMD 100 includes a main body unit 110 including the display units 152 and 154 for presenting information to the user, and an upper fixing unit 120 and a rear fixing unit 130 for fixing the main body unit 110 to the head. When the HMD 100 is fixed to the head of the user by the fixing units, the display units 152 and 154 of the main body unit 110 are located in front of the left and right eyes of the user.

The main body unit 110 is a portion that covers both the eyes of the user. The main body unit 110 may be configured so as to cover, for example, the parts in the vicinity of the left and right temples of the user. By forming the main body unit 110 into such a shape, it is possible to cover the parts in front of the eyes of the user almost perfectly when the user wears the HMD 100, and therefore, it is made possible for the user to easily view an image because no external light enters the user's eyes. It may also be possible to provide an image capturing unit 112 configured to photograph, for example, peripheral environment on the external surface of the main body unit 110. Due to this, the user wearing the HMD 100 can also recognize information on peripheral environment that is seen when the HMD 100 is not mounted (video see-through), in addition to information provided from the external device 400 etc. via the processor unit 200.

At an eyepiece plane 110a of the main body unit 110, as shown in FIG. 3, a first display unit 152 for the left eye and a second display unit 154 for the right eye are provided so as to correspond to the positions of the left and right eyes of the user. Between the first display unit 152 and the second display unit 154, for example, a cutout for positioning the nose of the user may be formed. A gap may be provided between the eyepiece plane 110a of the main body unit 110 and the user's eyes. By opening the lower part of the gap without covering it, the user may see his/her own hands etc. when the user lowers his/her visual line.

Inside the main body unit 110, a first display element (symbol 165 in FIG. 4) that presents an image for the left eye on the first display unit 152 and a second display element (symbol 166 in FIG. 4) that presents an image for the right eye on the second display unit 154 are provided. Each display element presents, for example, an image of the endoscope device provided by the processor unit 200, an image captured by the image capturing unit 112 of the main body unit 110, etc. Display control processing of an image that is displayed on the display unit of the HMD 100 will be described later. The main body unit 110 is also provided with a cable 140 that is connected to the processor unit 200 in order to perform transmission and reception of information with the processor unit 200. In the present embodiment, the HMD 100 and the processor unit 200 are connected by a wire, but the present disclosure is not limited to this example and communication of information between devices may be performed wirelessly.

The upper fixing unit 120 supports the main body unit 110 from the upper part of the head of the user in order to fix the main body unit 110 to the position of the user's eyes. The upper fixing unit 120 includes support units 121 and 124 located at the parietal region of the head, a first adjustment unit 122 configured to adjust the position on the user's front side and a second adjustment unit 125 configured to adjust the height position on the left and right sides of the user.

As shown in FIG. 2, the first adjustment unit 122 is a member that couples the upper part of the main body unit 110 and the support unit 121 and is configured so that the length thereof can be adjusted. By adjusting the length of the first adjustment unit 122, the degree with which a forehead contact pat 127 installed above the eyepiece plane 110a of the main body unit 110 is pressed against the forehead is changed, which enables to adjust the position on the user's front side.

As shown in FIG. 2, the second adjustment unit 125 is a member that couples both sides of the main body unit 110, which extend toward the upper part of the left and right ears of the user when the HMD 100 is mounted, and the support unit 124 and is configured so that the length thereof can be adjusted. The second adjustment units 125 are provided both on the left side and on the right side, respectively. By adjusting the length of the second adjustment unit 125, a head pat 122*a* installed between the first adjustment unit 122 and the head is pressed against the user's head and thereby the height positions of both the side parts of the main body unit 110 are adjusted.

The rear fixing unit 130 supports the main body unit 110 from the back of the user's head in order to fix the main body unit 110 at the position of the user's eyes. As shown in FIG. 2, the rear fixing unit 130 is a member that couples both sides of the main body unit 110 on the back side of the head and is configured so that the length thereof can be adjusted. By adjusting the length of the rear fixing unit 130, the degree with which side pats 126 provided on both sides of the main body unit 110 are pressed against the head is changed, which enables to adjust the support degree at the temporal region.

It may also be possible to switch information displayed on the display units 152 and 154 of the HMD 100 by a remote controller 102 (102A, 102B). The remote controller 102 is provided so as to form a pair with one HMD 100. For example, the remote controller may be a foot switch that a user steps on by the user's foot to perform an input operation. Input information from the remote controller 102 is output to the processor unit 200.

The processor unit 200 is a control device that controls connected devices. In the present embodiment, the processor unit 200 controls the HMDs 100 (100A, 100B), the display 300, and the external devices 400 (400A, 400B) as shown in FIG. 1. Specifically, the processor unit 200 processes information input from the external device 400 into information that can be displayed on the display devices of the HMDs 100 and the display 300 and outputs the information to each display device. Further, the processor unit 200 switches information displayed on the display units 152 and 154 of the HMD 100 based on the operation input from the remote controller 102 of each HMD 100.

The display 300 is a display device for an unspecified user to view information. The display 300 is mainly used for a user not wearing the HMD 100, who works together with users each wearing the HMD 100, to view information. The display 300 can display input information from the external device 400 and other pieces of information. Information displayed on the display 300 is set by a user or the processor unit 200.

The external device 400 is device that outputs information displayed on the display device, such as the HMD 100 and the display 300. In the endoscope system 1 of the present embodiment, for example, the external device 400A is an endoscope device and an image captured by the camera of the endoscope device is output to the processor unit 200.

In the endoscope system 1 such as this, information input from the external device 400 is processed by the processor unit 200 and is displayed on the display device, such as the HMD 100 and the display 300.

(1.2 Display Control Processing)

A user wearing the HMD 100 performs an operation while switching between medical image of the endoscope device etc. presented by the processor unit 200 and an image captured by the image capturing unit 112 of the HMD 100. At this time, on the display units 152 and 154 of the HMD 100, pieces of information visually recognized by users of other HMDs 100 whose display is controlled by the processor unit 200 are also displayed. Hereinafter, based on FIG. 4 to FIG. 7, display control processing in the endoscope system 1 according to the present embodiment will be described.

(1.2.1. Function Configuration)

FIG. 4 shows a function configuration of the HMD 100 and the processor unit 200 constituting the endoscope system 1 according to the present embodiment. In FIG. 4, only the function units that function when display control of the display units 152 and 154 of the HMD 100 is performed are shown and it is assumed that other function units are also included actually. In the example in FIG. 4, the processor unit 200 functions as a display control device that performs display control of the two HMDs 100A and 100B and based on instructions to switch displays of each of the HMDs 100A and 100B, information presented on each of the HMDs 100A and 100B is switched.

First, referring to the display processing functions of the HMD 100, as shown in FIG. 4, the HMD 100 includes a display port 162, an image generation unit 164, and the display elements 165 and 166.

The display port 162 is an interface that receives input information from the processor unit 200. To the display port 162, the cable 140 that enables information communication with the communication unit 200 is connected. Information input from the display port 162 is output to the image generation unit 164.

The image generation unit 164 generates image signals that are output to the display elements 165 and 166, respectively, based on the information acquired via the processor unit 200. In the case where the image presented to a user is a 3D image, the image generation unit 164 performs shift processing to produce a shift between a left-eye image signal that is output to the first display element 165 and a right-eye image signal that is output to the second display element 166. In the shift processing, for example, the amount of shift between the left-eye image signal and the right-eye image signal is determined in accordance with, for example, the distance between the display elements 165 and 166 and the user's eyes, the interval between user's eyes, the virtual image position, etc. The image generation unit 164 outputs the generated image signal to the first display element 165 and the second display element 166.

The display elements 165 and 166 emit image light toward the display units 152 and 154 based on the image signal input from the image generation unit 164. The display elements 165 and 166 are arranged, for example, so as to face the display units 152 and 154 in the longitudinal direction of the user's face when the HMD 100 is mounted. Due to this, the optical axis of the image light emitted from the display elements 165 and 166 and the display units 152 and 154 will become substantially parallel to the direction of the visual line when the use faces the front.

The display elements 165 and 166 include, for example, an organic electroluminescence (EL) element. By adopting the organic EL element as the display elements 165 and 166, it is possible to realize compactness, high contrast, quick responsiveness, etc. The display elements 165 and 166 have a configuration in which, for example, a plurality of red organic EL elements, a plurality of green organic EL elements, a plurality of blue organic EL elements, etc., are arranged in the form of a matrix. Each of these elements spontaneously emits light at predetermined timing, luminance, etc., by being driven by a drive circuit of active matrix type, passive matrix type, etc. By controlling the drive circuit based on the image signal generated in the image generation unit 164, a predetermined image is displayed on the entire display elements 165 and 166 and the display is presented to a user via the display units 152 and 154.

Between the display elements 165 and 166 and the display units 152 and 154, as an optical system, for example, a plurality of eyepiece lenses (not shown) may be arranged, respectively. By causing these eyepiece lenses and the user's eyes to face each other with a predetermined distance in between, it is made possible to cause a user to observe a virtual image, which seems to be an image displayed at a predetermined position (virtual image position). By presenting such a virtual image, it is possible to provide a 3D image. The virtual image position and size of the virtual image are set by the configuration etc. of the display elements 165 and 166 and the optical system.

In order to cause a user to observe a virtual image, the main body unit 110 is mounted on the user so that image light emitted in the optical axis direction from the display elements 165 and 166 forms an image on the retina of the left and right eyes, respectively. In the case where the main body unit 110 is not mounted appropriately, the image will be a blurred image out of focus or a deviation occurs in the 3D image, and therefore, a user is not able to view a desired image. Consequently, when wearing the HMD 100, a user fixes the main body unit 110 to the head by the upper fixing unit 120 and the rear fixing unit 130 so that relevant position is not shifted after adjusting the main body unit 110 to an appropriate position.

Next, referring to the display processing functions of the processor unit 200, as shown in FIG. 4, the processor unit 200 includes an image input unit 211, an image processing unit 212, a display control unit 213, an output unit 214, and an operation input unit 215.

The image input unit 211 is an interface that receives an image input to the processor unit 200 from the external device 400. In the example in FIG. 4, the endoscope device 10 is shown as the external device 400, and at this time, to the image input unit 211, an image captured by the camera (not shown) of the endoscope device 10 is input. The image input unit 211 outputs the input image to the image processing unit 212.

The image processing unit 212 processes an image input to the processor unit 200 into an image to be displayed on the HMD 100. The image processing unit 212 generates a left-eye image to be displayed on the first display unit 152 of the HMD 100 and a right-eye image to be displayed on the second display unit 154 from, for example, an image captured by the camera of the endoscope device 10. The image on which image processing has been performed by the image processing unit 212 is output to the display control unit 213.

The display control unit 213 controls information to be displayed on the display units 152 and 154 of the HMD 100. In the present embodiment, an image selected by a user of the HMD 100 is displayed on the display units 152 and 154 of the HMD 100 and at the same time, pieces of information viewed by other users each wearing the HMD 100 are also displayed. Due to this, it is possible for a user even when wearing the HMD 100 to recognize what other users are viewing, which enables to improve communication between users. Details of the display processing by the display control unit 213 will be described later. After determining information to be displayed on each HMD 100, the display control unit 213 outputs relevant information to each HMD 100 via the output unit 214.

The operation input unit 215 is an input unit that receives an operation input from a user. In the present embodiment, information to be displayed on the display units 152 and 154 of the HMD 100 can be switched by the remote controller 102. An operation input to the remote controller 102 is output to the operation input unit 215 and the operation input unit 215 outputs the operation input information to the display control unit 213. The display control unit 213 outputs specified information to the HMD 100 via the output unit 214 based on instructions to switch displays from the remote controller 102. At this time, the display control unit 213 manages the information currently displayed on each HMD 100 controlled by the processor unit 200. For example, the display control unit 213 may store information for identifying information displayed on each HMD 100 in a memory (not shown).

(1.2.2 Screen Display of HMD)

In the endoscope system 1 as shown in FIG. 4, the display control unit 213 causes the display units 152 and 154 to display pieces of information that other users each wearing HMD 100 are viewing as well as displaying an image selected by a user of the HMD 100. At this time, the display control unit 213 causes pieces of information that other users are viewing to be displayed at a position that will not make the image that the user him/herself is viewing difficult to view. FIG. 5 to FIG. 7 show examples of display information 500 displayed on the display units 152 and 154 of the HMD 100. In these examples, there are four users each wearing the HMD 100 and the processor unit 200 performs display control of each HMD 100.

As a display example of the display information 500 displayed on the display units 152 and 154 of the HMD 100, it may also be possible to present thumbnails of information that other users are viewing, for example, as shown in FIG. 5. For a user who works while wearing the HMD 100, information selected by relevant user (in the present embodiment, camera image of the endoscope device 10) is displayed in the entire display region as the main information. At this time, thumbnails 510, 520, and 530 of the pieces of information that the other users are viewing are displayed in part of the display region. The thumbnails 510, 520, and 530 are arranged and displayed in a row, for example, at the end part so as not to block the display of the main display information 500.

Further, it may also be possible to display identifiers 512, 522, and 532 corresponding to the thumbnails 510, 520, and 530, respectively, so as to indicate that on which HMD 100 each thumbnail is displayed. At this time, the identifiers 512, 522, and 532 are associated with the HMDs 100 and users who use the HMDs 100 in advance, thus making it possible for the user to grasp who is viewing which image by recognizing the relationship of correspondence in advance.

In the example in FIG. 5, the user wearing the HMD 100 with an identifier "1" views the same camera image of the endoscope device 10 as the image that the user views and the user wearing the HMD 100 with an identifier "2" views external image showing peripheral environment. The user wearing the HMD 100 with an identifier "3" views image (e.g., echo image) acquired by another medical instrument. In this manner, by making it possible to grasp what the other users view, it is made possible to have a conversation, give instructions, etc., while grasping the states of the other users, and therefore, communication is made easy to establish and the loss in cooperation in work can be eliminated.

At this time, in place of the identifiers 512, 522, and 532 that are displayed together with the thumbnails 510, 520, and 530 of pieces of information that the other users view, it may also be possible to display, for example, role names 514, 524, and 534 of the users as shown in FIG. 6. In the example shown in FIG. 6, the upper thumbnail 510 is information that an operator views, the middle thumbnail 520 is information that a person who operates the camera of the endoscope (scopist) views, and the lower thumbnail 530 is information that an assistant views. In this manner, by explicitly displaying the roles, it is possible to present information to the user in an easy-to-understand manner.

Further, as another example, it may also be possible to display charts 540, 550, and 560 as objects that represent pieces of information the other users view as shown in FIG. 7 in place of the thumbnails 510, 520, and 530. For example, the charts 540 and 550 in FIG. 7 indicate that the users view the image by the camera of the endoscope device 10 and the chart 560 indicates that the user views the image by the image capturing unit 112 provided on the main body unit 110 of the HMD 100. By representing pieces of information that the users view by the charts 540, 550, and 560 such as those, it is possible to let the user to know what the other users view in an intuitive manner.

Alternatively, it may also be possible to represent the users viewing the contents of these charts 540, 550, and 560 by user names 542, 552, and 562 together with the charts 540, 550, and 560. Due to this, it is possible to present information to the user in an easy-to-understand manner.

Other than the display examples shown in FIG. 5 to FIG. 7, it may also be possible to display the pieces of information that the other users view by pieces of text information, such as "Medical image A", "Medical image B", and "External image".

The pieces of information that the other users view, such as the thumbnails 510, 520, and 530 displayed on the display units 152 and 154, may be changed, for example, at timing when each user switches displays. At this time, in order to notify the user of that the display is switched to another, it may also be possible to, for example, cause the display of the thumbnail to blink temporarily, or to display an alarm for notifying the user of that the display is switched to another in the display region together with the identifier (or user name, user's role, etc.) of the HMD 100 in which the display is switched to another.

Further, the pieces of information that the other users view, such as the thumbnails 510, 520, and 530, are displayed so as not to make the main display information 500 less easy-to-see. For example, it may also be possible to display the thumbnail in a semitransparent manner so that the display information 500 can be visually recognized. Alternatively, it may also be possible to enable the user to change the display position of the thumbnail in the display region appropriately. By making it possible to adjust the display method and the display position of the thumbnail, it is possible to improve the visibility of the display information 500.

(1.3. Summary)

As above, the method for presenting information displayed on the HMD 100 in the endoscope system 1 according to the present embodiment is described. According to the present embodiment, in the circumstances where there exists a plurality of users each wearing the HMD 100, on the display units 152 and 154 of the HMD 100 of each user, pieces of information that the other users view are also displayed together with the main display information. Due to this, each user can grasp what the other users who are working in collaboration are viewing at present during the work. In such circumstances, a conversation is made and instructions are given, and therefore, it is made possible to easily establish communication between users and the occurrence of loss in cooperation etc. can be avoided.

2. Second Embodiment

Next, based on FIG. 8, display control in a system that uses an HMD according to a second embodiment of the present disclosure is described. In the present embodiment, the endoscope system is described as an example, as in the first embodiment. FIG. 8 is a function block diagram showing a function configuration of the HMD 100 and the processor unit 200 constituting the endoscope system 1 according to the present embodiment. FIG. 8 shows only the function units that function when display control of the display units 152 and 154 of the HMD 100 is performed, but it is assumed that other function units are included actually.

In the example in FIG. 8 also, as in FIG. 4 of the first embodiment, the processor unit 200 functions as the display control device that performs display control of the two HMDs 100A and 100B and switches information that is presented to each HMD based on instructions to switch displays of each of the HMDs 100A and 100B. The configuration of the endoscope system 1 according to the present embodiment differs from the configuration of the first embodiment shown in FIG. 4 in that the HMD 100 includes a visual line detection unit 167. The other function units are the same as those of the first embodiment, and therefore, description of these function units is omitted.

The visual line detection unit 167 provided in the HMD 100 detects the visual line of a user wearing the HMD 100. The visual line detection unit 167 captures an image of the eyes of the user wearing the HMD 100 and detects the visual line from the positional relationship between a reference point and a moving point in the eyes. The visual line of the user detected by the visual line detection unit 167 is output to the processor unit 200.

By detecting the visual line of the user by the visual line detection unit 167, for example, it is possible to grasp whether or not the user views the display units 152 and 154 of the HMD 100. When there is a gap between the main body unit 110 and the eyes of the user and the lower part thereof is opened as in the HMD 100 shown in FIG. 2, there is a case where the person wearing the HMD 100 is able to view something other than the information displayed on the display units 152 and 154. At this time, if the user notifies another user of the information displayed on the display units 152 and 154, the recognition differs between the users and circumstances where communication is not established smoothly are conceivable.

Further, for example, as in PinP (Picture In Picture), in the case where within the display region of the display units 152 and 154, another display region for displaying information is provided, the user moves his/her visual line to gaze the information in each display region. At this time, if the user notifies another user of the information displayed in the display region that the other user does not view, recognition will also differ between the users.

As described above, the information that a user visually recognizes is not necessarily limited to the main information displayed on the display units 152 and 154 of the HMD 100. Information that a user visually recognizes includes, for example, information when the user views his/her hand(s) and information in one of display regions in the case where a plurality of display regions exists in the display units 152 and 154, other than the main information displayed on the display units 152 and 154. Consequently, as in the present embodiment, the visual line detection unit 167 is provided in the HMD 100 and information that a user visually recognizes is specified from the visual line of the user. Due to this, it is made possible to more exactly notify another user of the information that the user views, and therefore, it is possible to improve the communication between the users.

As above, the method for presenting information displayed on the HMD 100 in the endoscope system 1 according to the present embodiment is described. According to the present embodiment, in the circumstances where there exists a plurality of users each wearing the HMD 100, pieces of information that the other users view are also displayed on the display units 152 and 154 of the HMD 100 of each user together with the main display information. At this time, by detecting the visual line of the user wearing the HMD 100 also, it is possible to more exactly recognize the information the user views. Due to this, it is made possible for each user to grasp what the other users who are working in collaboration are viewing during the work. In such circumstances, a conversation is made and instructions are given, and therefore, it is made possible to easily establish communication between users and the occurrence of the loss in cooperation can be avoided.

3. Modified Examples

In the above-described embodiments, communication between users each wearing the HMD 100 is described mainly, but the present disclosure is not limited to those examples. For example, the information that each user views may be displayed also on the display 300 connected to the processor unit 200. For example, as shown in FIG. 9, main display information 600 and information that each user wearing the HMD 100 views may be displayed on the display 300.

The display 300 is made use of, for example, mainly as a display device that a worker not wearing the HMD 100 views of the workers who are working in collaboration. It is difficult to recognize what the worker wearing the HMD 100 is viewing during his/her work from outside. Consequently, by displaying information that the worker wearing the HMD 100 is viewing on the display, it is made possible for the worker not wearing the HMD 100 also to recognize the information that the worker wearing the HMD 100 is viewing. Due to this, it is possible to more easily establish communication between the workers.

On the display 300, for example, as shown in FIG. 9, the main display information 600 set in advance, such as camera image of the endoscope device 10, is displayed in the entire display region and at the same time, pieces of information that the persons each wearing the HMD 100 view are displayed in part of the display region. The pieces of information that the persons each wearing the HMD 100 may be displayed as thumbnails 610, 620, and 630 of relevant information as shown in FIG. 5. Further, together with the thumbnails 610, 620, and 630, identifiers 612, 622, and 632 may also be displayed so that it is known on which HMD 100, the displayed information is displayed. At this time, the identifiers 612, 622, and 632 are associated with the HMDs 100 and the users who use the HMDs 100 in advance and by recognizing the relationship of correspondence, the user can grasp who views which image.

The display of the display 300 may be a display in which information that a person wearing the HMD 100 views is displayed as an object or text information as shown in FIG. 6 or FIG. 7 other than the example. Further, as information for identifying a person who views the information, the role or user name may be displayed other than the identifier.

As above, the preferred embodiments of the present disclosure are described in detail with reference to the appended drawings, but the technical scope of the present disclosure is not limited to those examples. It is obvious that a person with ordinary knowledge in the technical field of the present disclosure may think out various kinds of altered examples or modified examples in the category of the scope of the technical idea described in the claims and those are of course construed to be included in the technical scope of the present disclosure.

For example, in the above-described embodiments, the display control unit configured to control the information displayed on the HMD 100 or the display 300 is provided in the processor unit 200, but the present technology is not limited to those examples. For example, it may also be possible to provide all or part of the functions of the display control unit in each HMD 100.

Further, in the above-described embodiments, the organic EL element is used as the display element, but the present technology is not limited to those examples. For example, a liquid crystal display element (LCD) may be used as the display element.

Furthermore, in the above-described embodiments, in the circumstances where there exists a plurality of users each wearing HMD 100, the endoscope system 1 is taken as an example and communication between workers during the operation is described, but the present technology can be applied to other circumstances. For example, the present technology can be applied to a game that is played among a plurality of users each wearing the HMD 100.

The effects described in the present specification are only explanatory or illustrative but not limitative. The technology according to the present disclosure may bring about other effects obvious to the persons in the art from the description of the present specification together with the above-described effects or in place of the above-described effects.

Additionally, the present technology may also be configured as below.

(1)

A display control device including:

a display control unit configured to display pieces of information which a plurality of users each wearing a head mounted display visually recognize, respectively, on a display unit that the respective users each wearing the head mounted display are able to visually recognize.

(2)

The display control device according to (1), wherein the display control unit displays main information selected by a user wearing the head mounted display in a display region of the display unit and displays, in a part of the display region, objects indicating pieces of information that the respective other users each wearing the head mounted display visually recognize.

(3)

The display control device according to (2), wherein the objects are thumbnails of images that the respective other users each wearing the head mounted display visually recognize.

(4)
The display control device according to (2) or (3),
wherein the objects are pieces of text information indicating pieces of information that the respective other users each wearing the head mounted display visually recognize.

(5)
The display control device according to any one of (2) to (4),
wherein the objects are charts indicating pieces of information that the respective other users each wearing the head mounted display visually recognize.

(6)
The display control device according to any one of (2) to (5),
wherein the display control unit displays, together with the object, identification information for identifying a user who visually recognizes information corresponding to the object.

(7)
The display control device according to any one of (2) to (6),
wherein the display control unit displays, in a part of the display region, a notification indicating that pieces of information that the respective other users each wearing the head mounted display visually recognize have changed.

(8)
The display control device according to any one of (1) to (7),
wherein the display control unit further displays information that a plurality of users each wearing the head mounted display visually recognize, in a part of a display region of a display device that a user not wearing the head mounted display are able to visually recognize.

(9)
The display control device according to any one of (1) to (8),
wherein the display control unit determines information that a user wearing the head mounted display visually recognizes based on detection information from a visual line detection unit configured to detect a visual line of the user.

(10)
The display control device according to any one of (1) to (9),
wherein pieces of information that the plurality of users visually recognize, respectively, include at least an image captured by an endoscope device.

(11)
A display device including:
a display unit; and
a display control unit configured to display pieces of information which a plurality of users each wearing a head mounted display visually recognize, respectively, on a display unit that the respective users each wearing the head mounted display are able to visually recognize.

(12)
The display device according to (11),
wherein the display device is a head mounted display.

(13)
A display control system including:
a plurality of head mounted displays; and
a display control device configured to control pieces of information displayed on the head mounted displays,
wherein the head mounted displays and the display control device are communicatively connected, and
wherein the display control device outputs information selected by a user wearing the head mounted display and pieces of information that the respective other users each wearing a head mounted display visually recognize to each of the head mounted displays.

Furthermore, the present technology may also be configured as below.

(1')
A system comprising:
circuitry configured to generate display data to be displayed by each of a plurality of head mounted displays configured to be worn by each of a plurality of users involved in a surgery based on information that the each of a plurality of users in the surgery visually recognizes.

(2')
The system of (1'), wherein
the circuitry is configured to generate, as at least a part of the display data, main information selected by a received user input for display by a first of the plurality of head mounted displays.

(3')
The system of (1') or (2'), wherein
the circuitry is configured to generate, as at least a part of the display data to be displayed by a first of the head mounted displays configured to be worn by one of the users involved in the surgery, an object corresponding to information that another of the users in the surgery visually recognize.

(4')
The system of (3'), wherein
the object is a thumbnail image corresponding to a piece of information displayed by the another of the head mounted displays.

(5')
The system of (3') or (4'), wherein
the object is a piece of text information corresponding to a piece of information that the another of the users in the surgery visually recognizes.

(6')
The system of any one of (3') to (5'), wherein
the objects is a chart corresponding to a piece of information that the another of the users in the surgery visually recognizes.

(7')
The system of any one of (3') to (6'), wherein
the display data includes identification information identifying the another of the users.

(8')
The system of any one of (2') to (7'), wherein
the circuitry is configured to generate, as at least a part of the display data to be displayed by a first of the head mounted displays configured to be worn by one of the users involved in the surgery, a notification indicating that a piece of information that another of the users in the surgery visually recognizes has changed.

(9')
The system of any of (1') to (9'), wherein
the circuitry is configured to generate second display data to be displayed by a display device that a user not wearing the head mounted display is able to visually recognize.

(10')
The system of any of (1') to (9'), wherein
the information includes a viewpoint in which a user wearing the at least one of the plurality of head mounted displays views at least one of the user's hands at a surgical site.
(11')
The system of any of (1') to (10'), wherein
the circuitry is configured to determine information that a user wearing at least one of the head mounted displays visually recognizes by detecting a sight line of the user.
(12')
The system of any of (1') to (11'), wherein
the information includes an image captured by an endoscope device.
(13')
A surgical endoscopic system comprising:
a plurality of head mounted displays;
circuitry communicatively connected to each of the head mounted displays and configured to control information displayed on each of the head mounted displays; and an endoscope device communicatively connected to the circuitry, wherein
the circuitry is configured to output information selected by a user involved in a surgery wearing one of the head mounted displays to the one of the head mounted displays and a piece of information that another user involved in the surgery wearing another of the head mounted displays visually recognizes to the one of the head mounted displays.
(14')
A display control device comprising:
circuitry configured to generate display data corresponding to a viewpoint of each of a plurality of users wearing a respective one of a plurality of head mounted displays to each of the plurality of head mounted displays.
(15')
A display device comprising:
a display; and
circuitry configured to control the display based on display data corresponding to a viewpoint of each of a plurality of users wearing a respective one of a plurality of head mounted displays.
(16')
The display device according to (15'),
wherein the display device is a head mounted display.
(17')
A system comprising:
a plurality of head mounted displays; and
circuitry communicatively connected to the plurality of head mounted displays and configured to control pieces of information displayed on the head mounted displays, wherein
the circuitry is configured output information selected by a user wearing one of the head mounted displays to the one of the head mounted displays and a piece of information that another user wearing another of the head mounted displays visually recognizes to the one of the head mounted displays.

REFERENCE SIGNS LIST 1 endoscope system
100 HMD
102 remote controller
110 main body unit
152 first display unit
154 second display unit
162 display port
164 image generation unit
165 first display element
166 second display element
167 visual line detection unit
200 processor unit
211 image input unit
212 image processing unit
213 display control unit
214 output unit
215 operation input unit
300 display
400 external device

The invention claimed is:

1. A system comprising:
circuitry configured to
generate display data to be displayed by each of a plurality of head mounted displays worn by each of a plurality of users involved in a surgery,
generate, as at least a part of the display data to be displayed by a first of the head mounted displays worn by one of the users involved in the surgery, an object corresponding to information that is at least partially displayed on a second head mounted display worn by another of the users involved in the surgery,
detect a sight line of the another of the users, and
determine a view of the another of the users views based on the detected sight line,
wherein the object is generated based on the determination of the view of the another of the users and comprises at least part of the view of the another of the users.

2. The system of claim 1, wherein
the circuitry is configured to generate, as at least a part of the display data, main information selected by a received user input for display by a first of the plurality of head mounted displays.

3. The system of claim 1, wherein
the display data to be displayed by a first of the head mounted displays comprises a thumbnail image corresponding to a piece of information displayed by the another of the head mounted displays.

4. The system of claim 1, wherein
the display data to be displayed by a first of the head mounted displays comprises a piece of text information corresponding to a piece of information associated with the another of the users in the surgery, the piece of information includes a name of the another of the users or a type of identification of the another of the users.

5. A surgical endoscopic system comprising:
a plurality of displays including a main body portion and a display portion located in front of a left eye and a right eye of each user involved in surgery;
circuitry communicatively connected to each of the displays and configured to control information displayed on each of the displays; and
an endoscope device communicatively connected to the circuitry, wherein
the circuitry is configured to
output information selected by a user involved in a surgery using one of the displays to the one of the displays,
generate display data corresponding to a viewpoint of each of a plurality of users wearing a respective one of a plurality of displays to each of the plurality of displays by determining a respective view of each of the plurality of users based on a detected sight line of each of the plurality of users, wherein the display data comprises at least part of the respective view of a particular user of the plurality of users, and display the display data on at least one of the displays associated with another user of the plurality of users.

6. A system comprising:

circuitry configured to generate display data to be displayed by each of a plurality of displays including a main body portion and display portion located in front of a left eye and a right eye of each of a plurality of users involved in a surgery, generate, as at least a part of the display data to be displayed by a first of the displays located in front of one of the users involved in the surgery, an object corresponding to information that is at least partially displayed on a second display located in front of another of the users involved in the surgery, detect a sight line of the another of the users, and determine a view of the another of the users views based on the detected sight line, wherein the object is generated based on the determination of the view of the another of the users and comprises at least part of the view of the another of the users.

7. The system of claim 6, wherein the circuitry is configured to generate, as at least a part, of the display data, main information selected by a received user input for display by a first of the plurality of displays.

8. The system of claim 7, wherein the circuitry is configured to generate, as at least a part of the display data to be displayed by a first of the displays located in front of one of the users involved in the surgery, a notification indicating that a. piece of information that is viewed by the another of the users in the surgery has changed.

9. The system of claim 6, wherein the display data to be displayed by a first of the displays comprises a thumbnail image corresponding to a piece of information displayed by the another of the displays.

10. The system of claim 6, wherein the display data to be displayed by a first of the displays comprises a piece of text information corresponding to a piece of information associated with the another of the users in the surgery, the piece of information includes a name of the another of the users or a type of identification of the another of the users.

11. The system of claim 6, wherein the display data to be displayed by a first of the displays comprises a chart corresponding to a piece of equipment used by the another of the users in the surgery.

12. The system of claim 6, wherein the display data includes identification information identifying the another of the users.

13. The system of claim 6, wherein the circuitry is configured to generate second display data to be displayed by a display device that a user not using the display is able to view.

14. The system of claim 6, wherein the information includes a viewpoint in which a user using the at least one of the plurality of displays views at least one of the user's hands at a surgical site.

15. The system of claim 6, wherein the circuitry is further configured to detect the sight line of the another of the users using a sight line detecting sensor disposed on the second display.

16. The system of claim 6, wherein the circuitry is further configured for each of the plurality of displays, display an identification of a person using the displays.

17. The system of claim 6, wherein the circuitry is further configured to generate, as at least a part of the display data to be displayed by a first of the displays by one of the users involved in the surgery, a notification indicating that a piece of information that is viewed by the another of the users in the surgery has changed, the notification being a blinking thumbnail image partially displayed by the first of the displays.

18. The system of claim 6, wherein the circuitry is further configured to determine the sight line of the another of the users by capturing an image of the eyes of the another of the users with the second display.

19. The system of claim 6, wherein the object comprises an image acquired by a medical instrument.

20. The system of claim 6, wherein the object comprises an image of an external peripheral environment of the surgery.

* * * * *